(12) United States Patent
Sterrett

(10) Patent No.: US 11,202,639 B2
(45) Date of Patent: *Dec. 21, 2021

(54) COMBINED FLIP CUTTER AND DRILL

(71) Applicant: Arthrex, Inc., Naples, FL (US)

(72) Inventor: Jerry Sterrett, Naples, FL (US)

(73) Assignee: Arthrex, Inc., Naples, FL (US)

( * ) Notice: Subject to any disclaimer, the term of this patent is extended or adjusted under 35 U.S.C. 154(b) by 391 days.

This patent is subject to a terminal disclaimer.

(21) Appl. No.: 15/349,128

(22) Filed: Nov. 11, 2016

(65) Prior Publication Data

US 2017/0056027 A1    Mar. 2, 2017

Related U.S. Application Data

(60) Continuation of application No. 14/516,084, filed on Oct. 16, 2014, now Pat. No. 9,526,510, which is a division of application No. 12/397,263, filed on Mar. 3, 2009, now Pat. No. 8,888,781, which is a continuation-in-part of application No. 12/114,599, filed on May 2, 2008, now Pat. No. 8,652,139.

(60) Provisional application No. 61/033,252, filed on Mar. 3, 2008, provisional application No. 60/915,607, filed on May 2, 2007.

(51) Int. Cl.
| | |
|---|---|
| *A61B 17/16* | (2006.01) |
| *A61B 1/317* | (2006.01) |
| *A61B 17/32* | (2006.01) |
| *A61B 17/34* | (2006.01) |
| *A61B 90/00* | (2016.01) |
| *A61B 17/29* | (2006.01) |

(52) U.S. Cl.
CPC ......... *A61B 17/1617* (2013.01); *A61B 1/317* (2013.01); *A61B 17/1635* (2013.01); *A61B 17/1662* (2013.01); *A61B 17/1675* (2013.01); *A61B 17/32002* (2013.01); *A61B 17/3472* (2013.01); *A61B 90/06* (2016.02); *A61B 2017/2927* (2013.01); *A61B 2090/062* (2016.02)

(58) Field of Classification Search
CPC ............ A61B 17/1617; A61B 17/1675; A61B 17/317
See application file for complete search history.

(56) References Cited

U.S. PATENT DOCUMENTS

| | | |
|---|---|---|
| 5,147,373 A | 9/1992 | Ferzli |
| 5,429,504 A | 7/1995 | Peltier et al. |
| | (Continued) | |

OTHER PUBLICATIONS

Opposition Decision for EP Patent No. 2098177, May 24, 2016.
(Continued)

*Primary Examiner* — Samuel S Hanna
(74) *Attorney, Agent, or Firm* — Blank Rome LLP

(57) ABSTRACT

A flip cutter and drill instrument and method of antegrade drilling and retrograde cutting using such an instrument. The flip cutter and drill instrument is provided with a drill which has a multi-blade configuration and which engages an inner tube or inner member of the instrument to articulate between at least a first "straight" position (for example, about parallel to the longitudinal axis of the instrument) when the instrument is in the drilling mode, and at least a second "flip" position (for example, a non-parallel position relative to the longitudinal axis of the instrument) when the instrument is in the cutting mode.

10 Claims, 6 Drawing Sheets

(56) References Cited

U.S. PATENT DOCUMENTS

| | | | |
|---|---|---|---|
| 5,431,671 A | 7/1995 | Nallakrishnan | |
| 5,649,947 A | 7/1997 | Auerbach et al. | |
| 5,928,239 A | 7/1999 | Mirza | |
| 5,941,706 A | 8/1999 | Ura | |
| 6,235,057 B1 | 5/2001 | Roger et al. | |
| 6,679,886 B2 | 1/2004 | Weikel | |
| 6,884,246 B1 | 4/2005 | Sonnabend et al. | |
| RE42,757 E * | 9/2011 | Kuslich | A61B 17/1617 606/80 |
| 2001/0034526 A1 | 10/2001 | Kuslich | |
| 2002/0032447 A1* | 3/2002 | Weikel | A61B 17/7061 606/86 R |
| 2002/0183758 A1 | 12/2002 | Middleton | |
| 2003/0135218 A1 | 7/2003 | Eckman | |
| 2004/0092936 A1 | 5/2004 | Miller et al. | |
| 2004/0092988 A1* | 5/2004 | Shaolian | A61B 17/1617 606/167 |
| 2004/0199166 A1* | 10/2004 | Schmieding | A61B 17/1617 606/79 |
| 2004/0210231 A1 | 10/2004 | Boucher et al. | |
| 2005/0240193 A1* | 10/2005 | Layne | A61B 17/1604 606/80 |
| 2005/0261684 A1 | 11/2005 | Shaolian et al. | |
| 2006/0195112 A1* | 8/2006 | Ek | A61B 17/1617 606/86 R |
| 2007/0233138 A1 | 10/2007 | Figueroa et al. | |
| 2007/0250067 A1* | 10/2007 | Schmieding | A61B 17/0401 606/96 |
| 2007/0276391 A1 | 11/2007 | Graves et al. | |
| 2008/0039852 A1* | 2/2008 | Schmieding | A61B 17/1675 606/88 |
| 2008/0172125 A1* | 7/2008 | Ek | A61F 2/3859 623/14.12 |
| 2008/0249481 A1 | 10/2008 | Crainich et al. | |
| 2008/0275512 A1 | 11/2008 | Albertorio et al. | |
| 2008/0306483 A1 | 12/2008 | Iannarone | |
| 2010/0076503 A1* | 3/2010 | Beyar | A61B 17/7097 606/86 R |
| 2010/0268237 A1 | 10/2010 | Carl et al. | |

OTHER PUBLICATIONS

Opposition Decision, EP Patent No. 1987786, Apr. 4, 2016.
EP Extended Search Report, EP Patent No. 2218411, Jul. 1, 2010.
Arthrex "ACL Reconstruction with FlipCutter", Screenshots showing availability of video, on Jan. 1, 2009.
Arthrex newsletter *Scope This Out* "A Technical Pearls Newsletter for Arthroscopists" Winter 2008-2009, vol. 10, No. 4, pp. 1-8.
Arthrex "Flipcutter", Screenshots showing availability date of Arthrex newsletters on Jul. 1, 2009 and Jan. 1, 2009 relating to Flipcutter.
Opposition filed by Smith & Nephew against corresponding EP 2098177 B1, dated Jul. 15, 2014.

\* cited by examiner

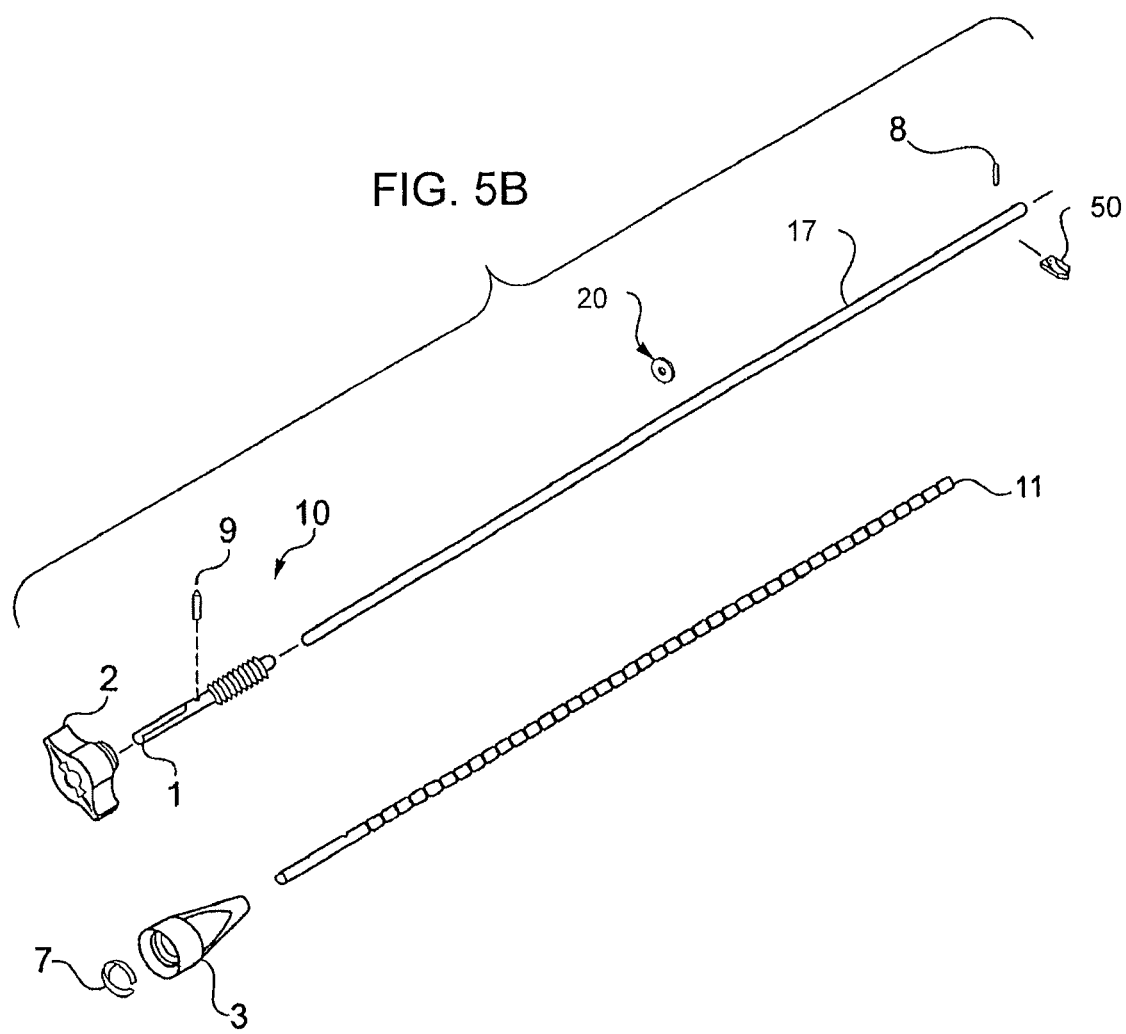

COMBINED FLIP CUTTER AND DRILL

CROSS-REFERENCE TO RELATED APPLICATIONS

This application is a continuation of U.S. application Ser. No. 14/516,084, filed Oct. 16, 2014, which is a divisional of U.S. application Ser. No. 12/397,263, filed Mar. 3, 2009, now U.S. Pat. No. 8,888,781, which claims the benefit of U.S. Provisional Application No. 61/033,252, filed Mar. 3, 2008, and which is a continuation-in-part of U.S. application Ser. No. 12/114,599, filed May 2, 2008, now U.S. Pat. No. 8,652,139, which in turn claims the benefit of U.S. Provisional Application No. 60/915,607, filed May 2, 2007, the entire disclosures of which are incorporated by reference herein.

FIELD OF THE INVENTION

The present invention relates to arthroscopic surgical methods and instruments and, more specifically, to a combined cutting and drilling instrument and methods of retrograde repairs and reconstructions.

BACKGROUND OF THE INVENTION

During arthroscopic surgery, a small incision is made in the skin covering the arthroscopic site or joint so that surgical instruments may be placed in the joint and manipulated through arthroscopic visualization. As only a very small incision is made during arthroscopic surgery, it is often difficult to handle instruments within the joint capsule, where visibility and access to the structures of the joint capsule is minimal. It is also difficult to manipulate instruments during the formation of a recipient site socket (for example, a femoral or tibial tunnel) during reconstructive surgery, with minimal bone loss and reduced intraarticular bone fragmentation of tunnel rims.

Accordingly, a need exists for a surgical drilling/cutting instrument that is configured to allow improved handling of the instrument within a joint capsule, for example the knee capsule, during ACL reconstruction. A need also exists for a surgical cutter that is stable during knee arthroscopy during the cutting mode, and that also provides drilling of femoral and tibial sockets or tunnels.

SUMMARY OF THE INVENTION

The present invention provides a combined flip cutter and drill instrument that is designed to function in both a drilling mode and a cutting mode. The flip cutter and drill of the present invention is provided with a cutting member with multiple cutting edges which engages the shaft of the instrument to articulate between at least a first "straight" position (for example, about parallel to the longitudinal axis of the instrument) and at least a second "flip" position (for example, a non-parallel position relative to the longitudinal axis of the instrument).

The combined flip cutter and drill of the present invention may be employed in a regular manner (when in the drilling mode, for example), or in a retrograde manner (when in the cutting mode, for example) to form a recipient socket (to accommodate an osteochondral transplant, or to allow retrograde fixation of a graft within two sockets, for example).

These and other features and advantages of the invention will be more apparent from the following detailed description that is provided in connection with the accompanying drawings and illustrated exemplary embodiments of the invention.

BRIEF DESCRIPTION OF THE DRAWINGS

FIGS. 5A and 5B illustrate another perspective view and an exploded view, respectively, of the combined flip cutter and drill of the present invention;

DETAILED DESCRIPTION OF THE PREFERRED EMBODIMENTS

Figures 1, 2, 3, 4:
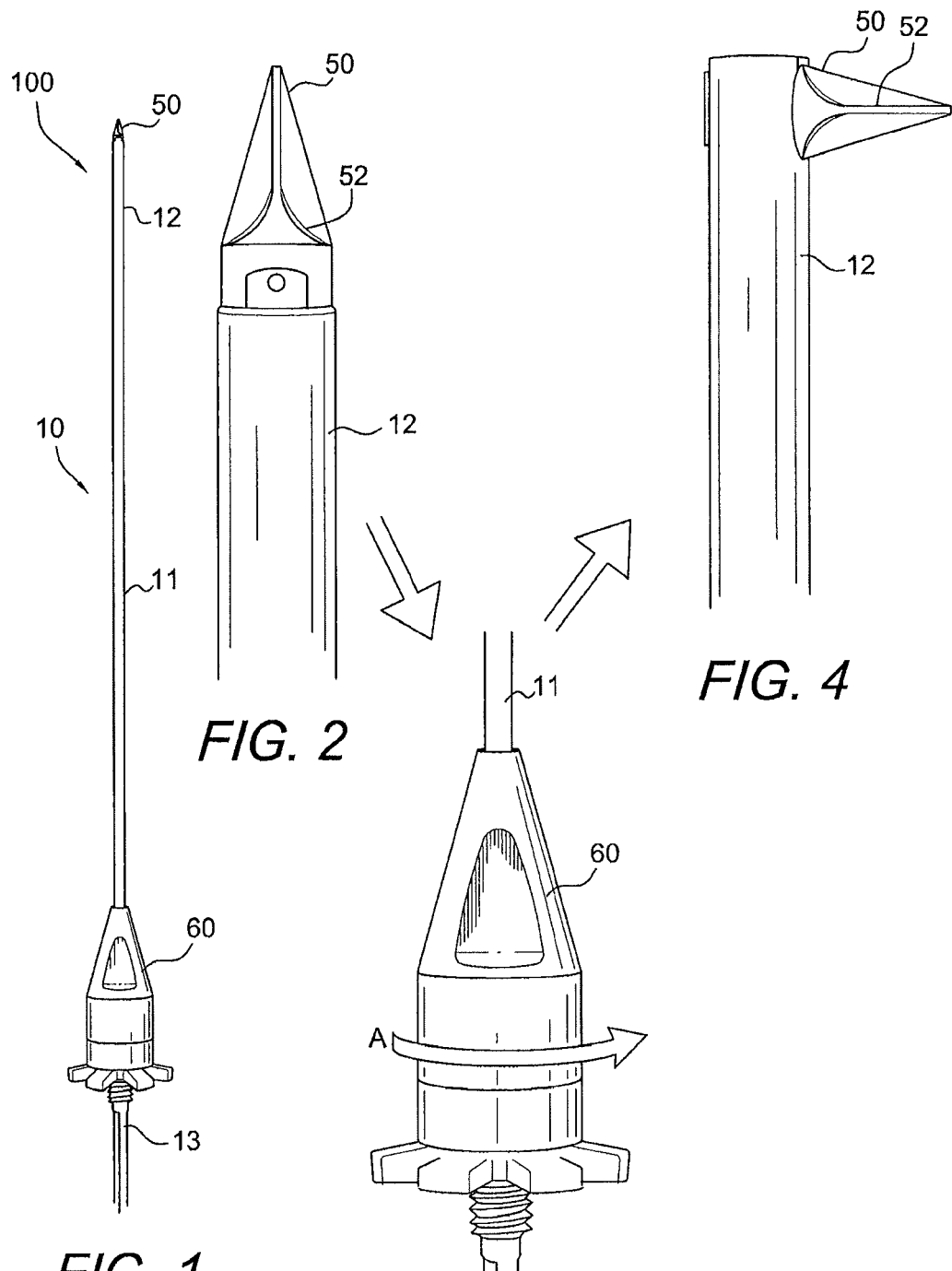
FIG. 1 illustrates a side view of the combined flip cutter and drill of the present invention.
FIG. 2 illustrates an enlarged view of the combined flip cutter and drill of FIG. 1, with the drill end in the "straight" (or drilling mode) configuration.
FIG. 3 illustrates an enlarged view of the actuating mechanism of the combined flip cutter and drill of FIG. 1.
FIG. 4 illustrates an enlarged view of the combined flip cutter and drill of FIG. 1, with the drill end in the "flip" (or cutting mode) configuration.

The following description is provided to enable any person skilled in the art to make and use the invention and sets forth the best modes contemplated by the inventors of carrying out their invention. Various modifications, however, will remain readily apparent to those skilled in the art.

The present invention provides a combined flip cutter and drill instrument that is designed to function in either a drilling mode or a cutting mode. The flip cutter and drill of the present invention is provided with a drill which has a conical, multi-blade configuration and which engages the shaft of the instrument to articulate between at least a first "straight" position (for example, about parallel to the longitudinal axis of the instrument) and at least a second "flip" position (for example, a non-parallel position relative to the longitudinal axis of the instrument).

The flip cutter and drill of the present invention may be employed in a regular manner (when in the drilling mode or "straight" position, for example), or in a retrograde manner (when in the cutting mode or "flip" position for example) to form a recipient socket (to accommodate an osteochondral transplant, or to allow retrograde fixation of a graft within two sockets, for example).

Referring now to the drawings, where like elements are designated by like reference numerals, FIGS. 1-8 illustrate various components of a combined flip cutter and drill 100 of the present invention. The flip cutter and drill 100 of the present invention is similar to the flip retrograde cutting instrument 100 of U.S. Pat. No. 8,652,139 (the disclosure of which is incorporated in its entirety herewith) but differs in that blade 5 of the flip retrograde cutter 100 is replaced by a drill or cutter 50 which is conical with a plurality of edges 52 (FIGS. 2 and 4) and/or has a plurality of blades with sharp cutting edges 52 (FIGS. 6-8), as described in more detail below, to allow drilling both in a regular manner (in an antegrade manner) and in a retrograde manner.

Figure 5A:
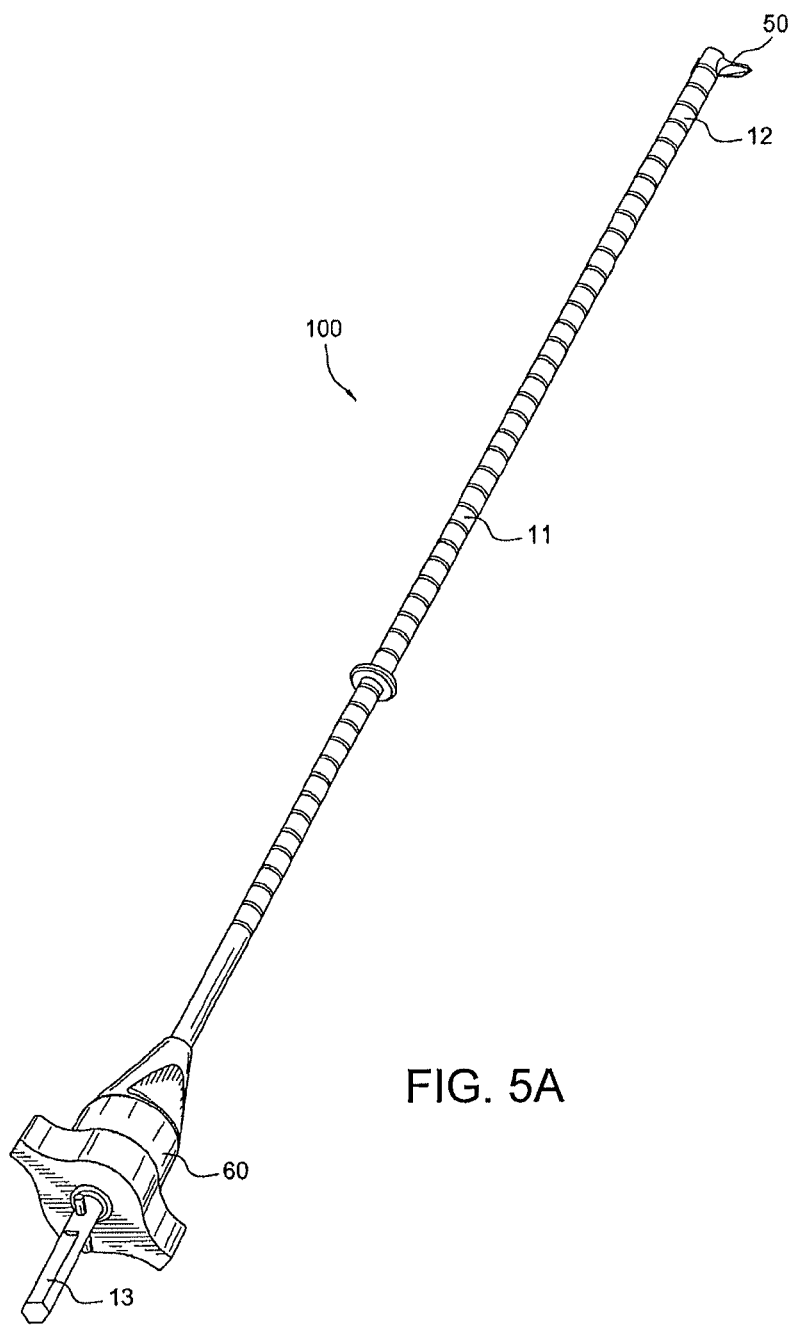

The flip cutter and drill 100 includes a cannulated elongated body 10 having a distal end 12 and a proximal end 13, as shown in FIGS. 1, 5A and 5B. The body 10 of the flip cutter and drill 100 includes a cannulated shaft or outer tube 11 provided at its distal end 12. The outer tube 11 houses an inner tube or inner member 17 (as shown in more detail in FIG. 8, for example) provided with a drill 50 having a plurality of cutting edges 52 (as shown in FIG. 2, for example). Details of specific exemplary embodiments of the drill 50 of the flip cutter and drill 100 are illustrated in FIGS. 2, 4 and 6-8; however, the invention contemplates other shapes and geometries for the drill 50.

Figure 6:
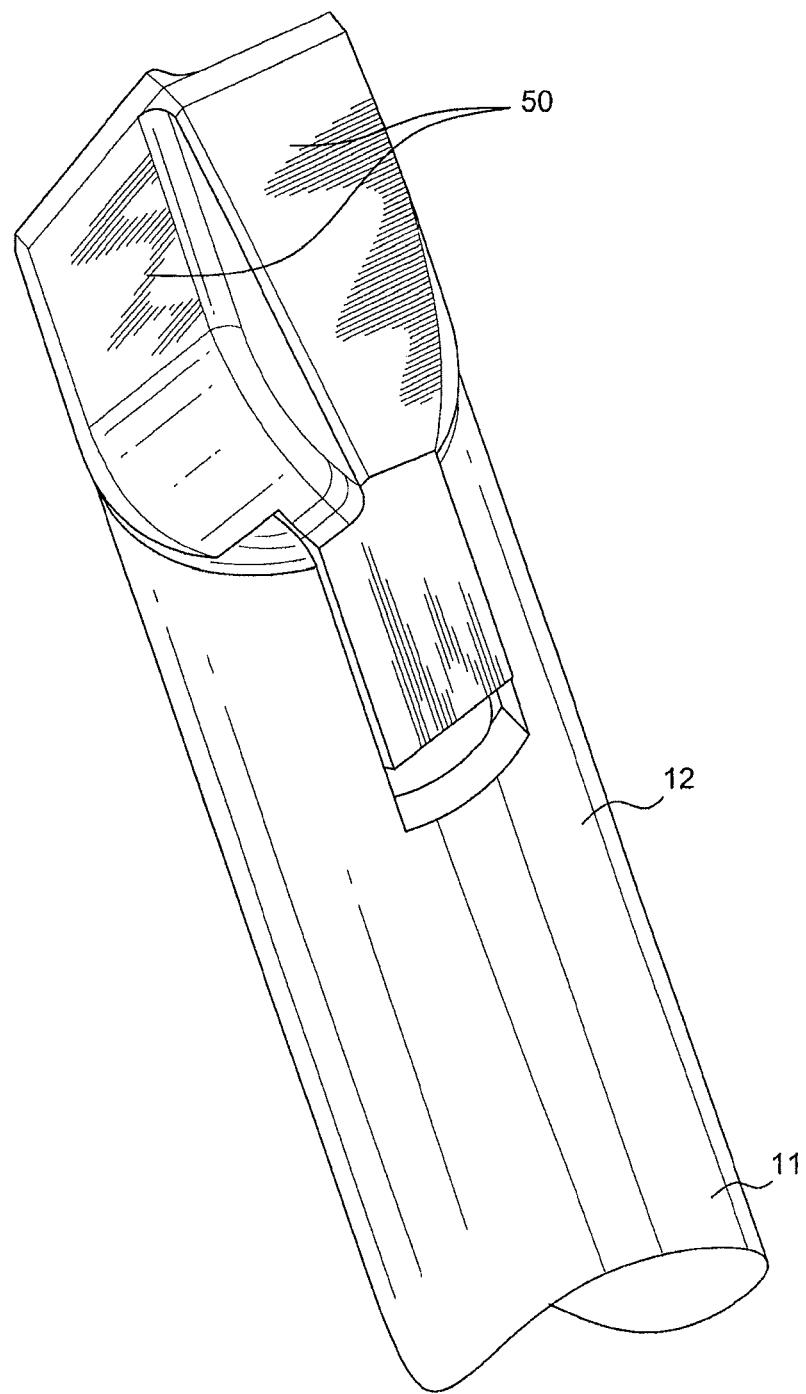
FIG. 6 illustrates an enlarged view of the distal end of the combined flip cutter and drill of FIG. 1, with the drill end in the "straight" (or drilling mode) configuration.

Drill 50 illustrated in detail in FIGS. 2, 4 and 6-8 is configured to engage the shaft or inner tube 17 of the instrument 100 and to articulate between at least first and second positions. In an exemplary embodiment, drill 50 engages inner tube 17 in a first or "straight" position (for example, about parallel to the longitudinal axis of the cutting instrument 100), as shown in FIGS. 1, 2 and 6. In the "straight" configuration, instrument 100 functions in the antegrade drilling mode.

Figure 7:
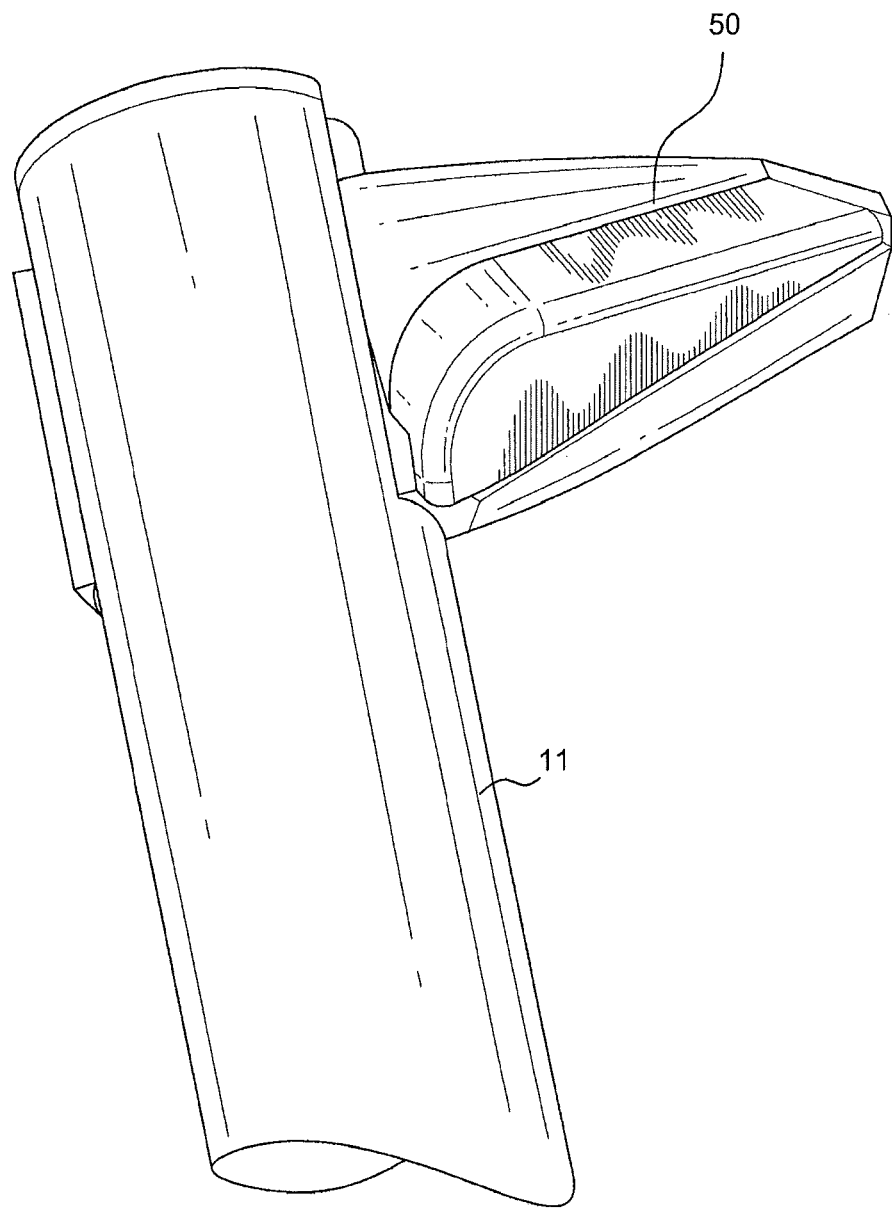
FIG. 7 illustrates an enlarged view of the distal end of the combined flip cutter and drill of FIG. 1, with the drill end in the "flip" (or cutting mode) configuration.
Figure 8:
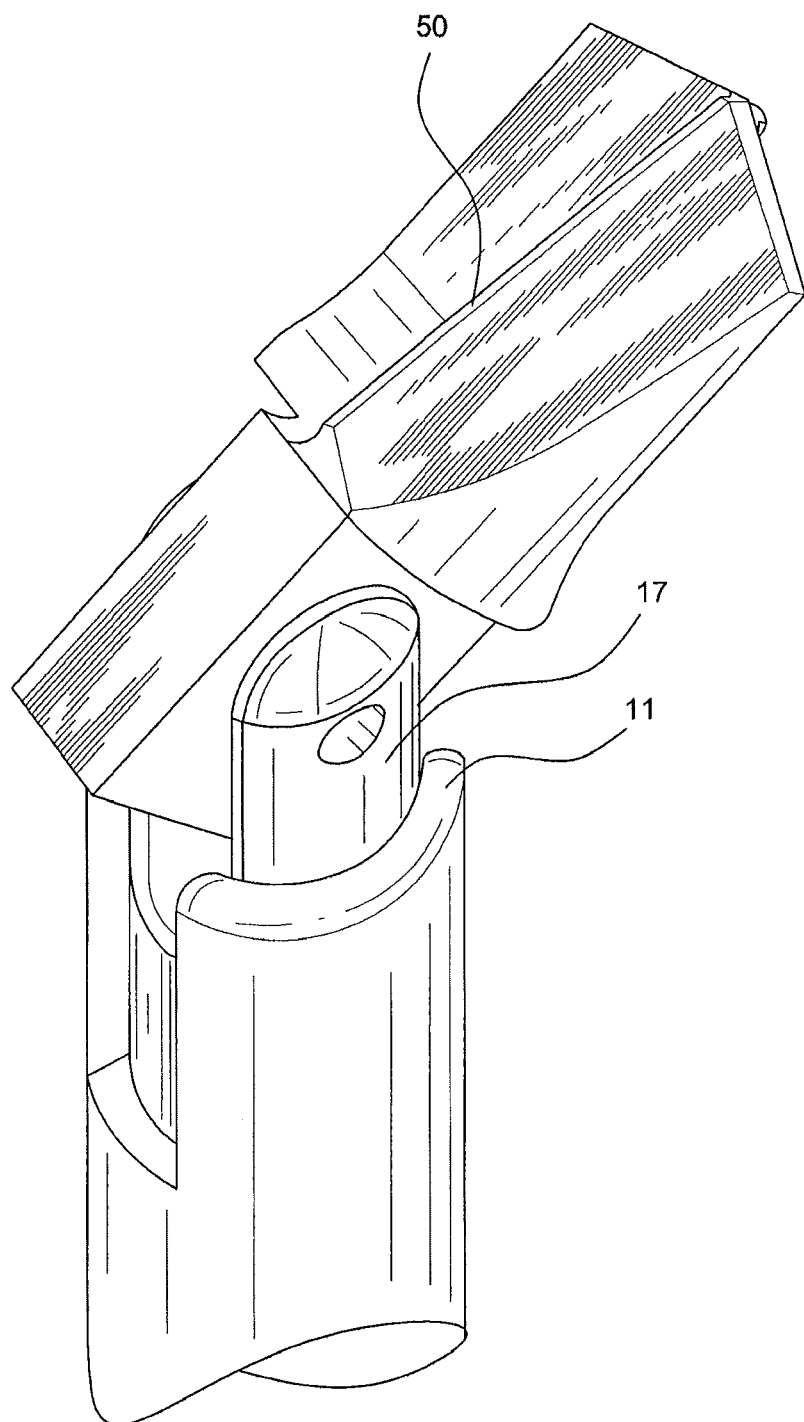
FIG. 8 illustrates an enlarged view of the distal end of the combined flip cutter and drill of FIG. 1, with the outer tube in a retracted position to show the pivoting axis.

In an exemplary embodiment, drill 50 engages the shaft of the instrument in a second or "flip" position (for example, a non-parallel position relative to the longitudinal axis of the cutting instrument 100), as shown in FIGS. 4, 5A, 5B and 7. In the "flip" configuration, instrument 100 functions in the cutting mode (for example, retrograde cutting). The non-parallel position shown in FIGS. 4, 5 and 7 is about perpendicular to the longitudinal axis of the cutting instrument 100; however, the present invention contemplates embodiments wherein drill 50 forms any angle with the shaft (for example, an angle between about 10 to about 170 degrees relative to the longitudinal axis of the cutting instrument 100, as shown in FIG. 8, for example).

In use, once the drilling/cutting instrument 100 is inserted into a joint, for example, a knee joint, the surgeon rotates (in the direction of arrow "A" of FIG. 3) actuating mechanism 60 to pivot the cutting drill 50 into the "flip" configuration (i.e., into a position other than the "straight" position), wherein the cutting tip is disposed at an angle of about 90 degrees with respect to the shaft of the instrument. The surgeon may also gradually increase or decrease the angle, as desired and in accordance with the characteristics of the surgical site. Once the drill is articulated in the desired "flip" position, the drill is preferably locked in position by tightening the tube 11. A drilling operation (when the instrument is in the "straight" position) or a retrograde cutting operation (when the instrument is in the "flip" position) may be subsequently carried, as desired and as known in the art.

As seen in FIGS. 5A and 5B, actuating mechanism 60 comprises a driver end 1, a nut 2, a hub 3, a retainer ring 7, two pins (a slotted spring pin 9 and a pin 10), and the shaft 11. The flip cutter and drill 100 is preferably assembled by first pressing the shaft 11 into the hub 3 until the shaft 11 bottoms out. The retainer ring 7 is then inserted into a groove of the hub 3 to form a first sub-assembly. Next, the inner member 17 is inserted into an end of the driver end 1 and securely engaged using the pin 10. The first sub-assembly, described above, is slid over the assembled inner member 17 and driver end 1. Next, the drill 50 is slid into slot of the inner member 17 and securely engaged using cross pin 8. The nut 2 is then screwed onto the other end of the driver end 1. Next, the hub 3 is pulled back while advancing the nut 2 until the retainer ring 7 engages and the slotted spring pin 9 is inserted into a through hole in the driver end 1 to secure the driver end 1 against the nut 2. An O-Ring 20 may be slid over the shaft 11, having laser etches on its circumference. The O-Ring 20 may be used to measure depth during retrograde drilling.

The present invention may be used to faun various sockets or tunnels to allow fixation of a graft (for example, a semitendonosus allograft) or to allow replacement of osteochondral cores or implants in a retrograde manner, to obviate inserting harvesters into the joint. For example, drilling/cutting instrument 100 of the present invention may be employed for the formation of sockets during an "all-inside ACL RetroConstruction™" for ligament repair, which may comprise, for example, the steps of: (i) drilling at least a femoral and tibial tunnel or socket using a retrograde drill technique employing the drilling/cutting instrument 100 of FIGS. 1-8; (ii) providing a graft (soft tissue graft or BTB graft) in the vicinity of the sockets; and (iii) securing the graft within the femoral and tibial tunnels (sockets).

According to yet another embodiment, an exemplary method of ACL RetroConstruction™ of the present invention comprises, for example, the steps of: (i) drilling a femoral socket; (ii) drilling a tibial tunnel or socket using a retrograde drill technique employing the drilling/cutting instrument 100 of FIGS. 1-8; (iii) providing a graft (soft tissue graft or BTB graft) in the vicinity of the sockets; (iv) securing the graft (soft tissue graft or BTB graft) to a continuous loop/button construct comprising a button with an oblong configuration and provided with an inside eyelet that allows the passage of the continuous loop, preferably a suture loop; (v) passing the graft with the button through the femoral tunnel; (vi) securing the button to the femoral cortex once the button exits the femoral socket; and (vii) securing the graft in the tibial tunnel or socket.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting. It is preferred, therefore, that the present invention be limited not by the specific disclosure herein, but only by the appended claims.

What is claimed is:

1. A method of a socket formation in a bone for a ligament reconstruction using a surgical instrument having a pivotable cutting device with at least one sharp cutting edge hingedly coupled to a cannulated shaft or an outer tube by a hinge, wherein the pivotable cutting device is pivotable between a first position and a second position about the hinge relative to the cannulated shaft or outer tube, comprising the steps of:

drilling a tunnel through the bone to a joint cavity in an antegrade manner with the surgical instrument by advancing the surgical instrument distally while rotating the surgical instrument about a longitudinal axis of the cannulated shaft or outer tube, with the pivotable cutting device being in the first position when drilling in the antegrade manner, in which the pivotable cutting member does not extend radially outside the cannulated shaft or the outer tube, until the pivotable cutting device reaches the joint cavity;

after drilling the tunnel in the antegrade manner, pivoting the pivotable cutting device to the second position while the pivotable cutting device is in the joint cavity such that the pivotable cutting device extends radially outside of the cannulated shaft or outer tube; and then drilling the bone in a retrograde manner with the surgical instrument by pulling the surgical instrument proximally through the tunnel while rotating the surgical instrument about the longitudinal axis of the cannulated shaft or outer tube, with the pivotable cutting device pivoted in the second position, so that the pivotable cutting device drills in the retrograde manner to form the socket in the bone facing the joint cavity, wherein the steps of drilling the tunnel in the antegrade manner and the drilling of the socket in the retrograde manner are performed sequentially without removing the pivotable cutting device from the joint cavity, wherein the pivotable cutting device remains coupled to the surgical instrument when drilling both in the antegrade manner and the retrograde manner.

2. The method of claim 1, wherein the pivotable cutting device is actuated from a proximal end of the surgical instrument to pivot from the first position to the second position.

3. The method of claim 1, wherein the pivotable cutting device includes a plurality of sharp cutting edges.

4. A method of a socket formation in a bone for a ligament reconstruction using a surgical instrument having a pivotable cutting device including at least one sharp cutting edge hingedly coupled to the surgical instrument by a hinge, wherein the pivotable cutting device is pivotable between a first position and a second position about the hinge, comprising the steps of:

antegrade drilling with the surgical instrument through the bone to a joint cavity in a first direction to form a tunnel in the bone by pushing the surgical instrument distally while rotating the surgical instrument about a longitudinal axis of the surgical instrument, with the pivotable cutting device being in the first position, in which the pivotable cutting device is aligned with the longitudinal axis of the surgical instrument, until the pivotable cutting device reaches the joint cavity;

after antegrade drilling the tunnel, with the pivotable cutting device in the joint cavity, pivoting the pivotable cutting device to the second position in which the pivotable cutting device is not aligned with the longitudinal axis of the surgical instrument, and in which the pivotable cutting device extends radially outside the surgical instrument; and subsequently retrograde drilling the bone by pulling the surgical instrument proximally in a second direction opposite the first direction through the tunnel while rotating the surgical instrument about its longitudinal axis and with the pivotable cutting device pivoted in the second position so that the pivotable cutting device drills in the retrograde manner to form the socket in the tunnel of the bone facing the joint cavity, wherein the antegrade drilling of the tunnel and the retrograde drilling of the socket are performed sequentially without removing the pivotable cutting device from the joint cavity, and wherein the pivotable cutting device remains coupled to the surgical instrument when both antegrade drilling and retrograde drilling.

5. The method of claim 4, wherein the pivotable cutting device includes a plurality of sharp cutting edges.

6. A method of a socket formation in a bone for a ligament reconstruction using a surgical instrument having a pivotable cutting device hingedly coupled to a shaft by a hinge, wherein the pivotable cutting device is pivotable between a first position and a second position about the hinge relative to the shaft, comprising the steps of:

drilling a tunnel through the bone to a joint cavity in an antegrade manner with the surgical instrument by advancing the surgical instrument distally while rotating the surgical instrument about a longitudinal axis of the shaft, with the pivotable cutting device being in the first position when drilling in the antegrade manner, in which the pivotable cutting member does not extend radially outside the shaft, until the pivotable cutting device reaches the joint cavity; and after drilling the tunnel in the antegrade manner, pivoting the pivoting cutting device to the second position while the pivotable cutting device is in the joint cavity such that the pivotable cutting device extends radially outside of the shaft; and then drilling the bone in a retrograde manner with the surgical instrument by pulling the surgical instrument proximally through the tunnel while rotating the surgical instrument about the longitudinal axis of the shaft, with the pivotable cutting device pivoted in the second position so that the pivotable cutting device drills in the retrograde manner to form the socket in the bone facing the joint cavity, wherein the pivotable cutting device remains coupled to the surgical instrument when drilling in the antegrade manner, when pivoting the pivotable cutting device to the second position while the pivotable cutting device is in the joint cavity, and when drilling in the retrograde manner.

7. The method of claim 6, wherein the shaft is cannulated.

8. The method of claim 6, wherein when drilling in the retrograde manner to form the socket, the socket has a depth that extends through only a portion of the bone.

9. The method of claim 6, wherein the pivotal cutting device includes a plurality of sharp cutting edges.

10. The method of claim 6, wherein the step of pivoting the pivotable cutting device to the second position while the pivotable cutting device is in the joint cavity includes pivoting the pivotable cutting device to about 90 degrees with respect to the longitudinal axis of the shaft.

* * * * *